United States Patent [19]
Keogh

[11] Patent Number: 6,033,719
[45] Date of Patent: Mar. 7, 2000

[54] METHOD FOR COVALENT ATTACHMENT OF BIOMOLECULES TO SURFACES OF MEDICAL DEVICES

[75] Inventor: James R. Keogh, Maplewood, Minn.

[73] Assignee: Medtronic, Inc., Minneapolis, Mich.

[21] Appl. No.: 09/012,056

[22] Filed: Jan. 22, 1998

Related U.S. Application Data

[63] Continuation-in-part of application No. 08/635,187, Apr. 25, 1996, Pat. No. 5,821,343, and a continuation-in-part of application No. 09/001,994, Dec. 31, 1997, Pat. No. 5,945,319, and a continuation-in-part of application No. 08/694,535, Aug. 9, 1996, Pat. No. 5,728,420, and a continuation-in-part of application No. 08/984,922, Dec. 4, 1997, Pat. No. 5,891,506.

[51] Int. Cl.$^7$ ............... B05D 3/10; A61L 33/00; A61L 27/00
[52] U.S. Cl. ............... 427/2.12; 427/2.13; 427/2.24; 427/2.3; 427/2.31; 427/337; 427/338; 427/342
[58] Field of Search .................. 427/2.1, 2.12, 427/2.13, 2.24, 2.28, 2.3, 2.25, 2.31, 337, 338, 342

[56] References Cited

U.S. PATENT DOCUMENTS

| | | | |
|---|---|---|---|
| 3,826,678 | 7/1974 | Hoffman et al. | 117/81 |
| 3,836,433 | 9/1974 | Wirth et al. | 195/68 |
| 4,003,846 | 1/1977 | Kuhn et al. | 427/340 |
| 4,115,548 | 9/1978 | Marsh et al. | 424/70 |
| 4,265,233 | 5/1981 | Sugitachi et al. | 128/156 |
| 4,284,553 | 8/1981 | Brown et al. | 427/220 |
| 4,375,399 | 3/1983 | Havas et al. | 204/195 B |
| 4,521,564 | 6/1985 | Solomon et al. | 525/54.1 |
| 4,600,652 | 7/1986 | Solomon et al. | 423/423.3 |
| 4,613,665 | 9/1986 | Larm | 536/20 |
| 4,642,242 | 2/1987 | Solomon et al. | 427/2 |
| 4,687,808 | 8/1987 | Jarrett et al. | 427/2.12 |
| 4,720,512 | 1/1988 | Hu et al. | 523/112 |
| 4,786,556 | 11/1988 | Hu et al. | 428/412 |
| 4,840,892 | 6/1989 | Adams et al. | 435/5 |
| 4,960,423 | 10/1990 | Smith | 623/1 |
| 5,002,884 | 3/1991 | Kobayashi et al. | 435/176 |
| 5,032,666 | 7/1991 | Hu et al. | 528/70 |
| 5,053,048 | 10/1991 | Pinchuk | 623/1 |
| 5,071,973 | 12/1991 | Keller et al. | 536/8 |
| 5,077,372 | 12/1991 | Hu et al. | 528/70 |
| 5,147,652 | 9/1992 | Egyud | 424/450 |
| 5,260,272 | 11/1993 | Donachy et al. | 427/384 |
| 5,308,641 | 5/1994 | Cahalan et al. | 427/2.25 |
| 5,344,455 | 9/1994 | Keogh et al. | 623/11 |
| 5,362,852 | 11/1994 | Geoghegan | 530/345 |
| 5,494,756 | 2/1996 | Siegel | 427/2.11 |
| 5,672,638 | 9/1997 | Verhoeven et al. | 427/2.25 |
| 5,817,303 | 10/1998 | Stedronsky et al. | 424/78.02 |
| 5,866,113 | 2/1999 | Hendriks et al. | 427/2.24 |

OTHER PUBLICATIONS

R.G. Dickinson et al., "A New Sensitive and Specific Test for the Detection of Aldehydes: Formation of 6–Mercapto–3–substitited–s–traizolo[4,3–b]–s–tetrazines", *Chem. Commun.*, 1719–1720 (1970).

K.F. Geoghegan et al., "Site–Directed Conjugation of Non–peptide Groups to Peptides and Proteins via Periodate Oxidation of a 2–Amino Alcohol. Application to Modification at N–Terminal Serine", *Bioconjugate Chem.*, 3, 138–146 (1992).

A.S. Hoffman et al., ACovalent Binding of Biomolecules to Radiation–Grafted Hydrogels on Inert Polymer Surfaces, @*Trans. Am. Soc. Artif. Intern. Organs*, 18, 10–18 (1972).

S. Holmes et al., AAmination of Ultra–high Strength Polyethylene using Ammonia Plasma,@*Composites Science and Technology*, 38, 1–21 (1990).

Y. Ito et al., AMaterials for Enhancing Cell Adhesion by Immobilization of Cell–Adhesive Peptide, @*J. Biomed. Mat. Res.* 25 1325–1337 91.

P.H. O=Farrel, AHigh Resolution Two–Dimensional Electrophoresis of Proteins,@*J. Biol. Chem.*, 250, 4007–4021 (1975).

*Primary Examiner*—Diana Dudash
*Attorney, Agent, or Firm*—Thomas F. Woods; Harold R. Patton

[57] ABSTRACT

A method for making a medical device having at least one biomolecule immobilized on a substrate surface is provided. The method may include combining a biomolecule comprising a 1,2 dicarbonyl moiety with a material comprising a guanidino moiety to form an immobilized biomolecule on a medical device biomaterial surface through covalent bonds. Another method of the present invention may include combining a biomolecule comprising a guanidino moiety with a material comprising a 1,2 dicarbonyl moiety to form an immobilized biomolecule on a medical device biomaterial surface through covalent bonds. Additionally, one method of the present invention may be employed to crosslink biomolecules, located in solution or on a medical device biomaterial surface, thereby forming a crosslinked biomaterial or a crosslinked medical device coating.

76 Claims, No Drawings

METHOD FOR COVALENT ATTACHMENT OF BIOMOLECULES TO SURFACES OF MEDICAL DEVICES

CROSS-REFERENCE TO RELATED APPLICATIONS

This application is a continuation-in-part of each of U.S. patent application Ser. Nos. 08/635,187, now U.S. Pat. No. 5,821,343, for "Oxidative Method for Attachment of Biomolecules to Surfaces of Medical Devices" filed Apr. 25, 1996; 09/001,994 for "Oxidative Method for Attachment of Biomolecules to Medical Device Surfaces" filed Dec. 31, 1997, now U.S. Pat. No. 5,945,319; 08/694,535 for "Oxidative Method of Attachment of Glyco-Proteins to Surfaces of Medical Devices" filed Aug. 9, 1996, now U.S. Pat. No. 5,728,428; 08/984,922 for "Oxidative Method of Attachment of Glyco-Proteins or Glyco-Peptides to Surfaces of Medical Devices" filed Dec. 4, 1997, now U.S. Pat. No. 5,891,506. All the foregoing patent applications are hereby incorporated by reference herein, each in its respective entirety. Additionally, U.S. patent application Ser. No. 09/010,906 entitled "Method of Ionic Attachment of Biomolecules to Surfaces of Medical Devices" to Keogh filed Jan. 22, 1998, now U.S. Pat. No. 5,928,916 is hereby incorporated herein its entirety.

BACKGROUND OF THE INVENTION

For many years, a number of medical devices (e.g., pacemakers, vascular grafts, stents, heart valves, etc.) that contact bodily tissue or fluids of living persons or animals have been developed, manufactured and used clinically. A major problem with such articles is that their surfaces tend to adsorb a layer of proteins from tissues and fluids such as tears, urine, lymph fluid, blood, blood products, and other fluids and solids derived from blood. The composition and organization of this adsorbed protein layer is thought to influence, if not control, further biological reactions. Adverse biological reactions such as thrombosis and inflammation may diminish the useful lifetime of many devices.

Implantable medical devices may serve as foci for infection of the body by a number of bacterial species. Such device-associated infections are promoted by the tendency of these organisms to adhere to and colonize the surface of the device. Consequently, it has been of great interest to physicians and the medical industry to develop surfaces that are less prone to promote the adverse biological reactions that typically accompany the implantation of a medical device.

One approach for minimizing undesirable biological reactions associated with medical devices is to attach various biomolecules to their surfaces. Biomolecules such as antithrombogenics, antiplatelets, anti-inflammatories, antimicrobials, growth factors, proteins, peptides, and the like have been used to minimize adverse biomaterial-associated reactions. A number of approaches have been suggested to attach such biomolecules. These approaches generally are covalent attachment techniques or ionic attachment techniques. Covalent attachment techniques typically require the use of coupling agents such as glutaraldehyde, cyanogen bromide, p-benzoquinone, succinic anhydrides, carbodiimides, diisocyanates, ethyl chloroformate, dipyridyl disulphide, epichlorohydrin, azides, among others, which serve as attachment vehicles for coupling of biomolecules to biomaterial surfaces. For example, covalent attachment of biomolecules using water soluble carbodiimides is described by Hoffman et al., "Covalent Binding of Biomolecules to Radiation-Grafted Hydrogels on Inert Polymer Surfaces," Trans. Am. Soc. Artif. Intern. Organs, 18, 10–18 (1972); and Ito et al., "Materials for Enhancing Cell Adhesion by Immobilization of Cell-Adhesive Peptide," J. of Biomed. Mat. Res., 25, 1325–1337 (1991).

One type of biomolecule which is coupled to biomaterial surfaces with coupling molecules is protein. Proteins are polypeptides made up of amino acid residues. A protein comprising two or more polypeptide chains is an oligomeric protein. In general, established coupling procedures couple proteins to substrate surfaces using coupling molecules which react with a protein's lysine amino acid residues which contain terminal amino groups. The use of coupling molecules may add instability to the biomaterial surface and increase the prospect for burial of the attached protein in the coupling layer. Coupling molecules may also create non-specific and undesirable crosslinks between protein molecules, thereby destroying the biological properties of the protein or they may create bonds amongst surface functional sites, thereby inhibiting attachment. The use of coupling molecules may also decrease the specificity for attachment of the protein to the biomaterial surface, thereby losing conformational control over the attachment process.

Thus, what is needed are alternative methods for attaching biomolecules to the substrate surface of a medical device, particularly methods that do not require the use of coupling molecules.

SUMMARY OF THE INVENTION

The present invention provides improved methods for covalently attaching a biomolecule to a substrate surface. More particularly, the present invention provides methods for making a medical device having at least one biomolecule covalently immobilized on a biomaterial surface. One method of the present invention includes combining at least one biomolecule comprising a 1,2 dicarbonyl moiety (RCOCOR') with a material comprising at least one guanidino moiety (R"NHC(NH)NH$_2$) to form an immobilized biomolecule on a medical device biomaterial surface through covalent bonds. A second method of the present invention includes combining at least one biomolecule comprising a guanidino moiety with a material comprising at least one 1,2 dicarbonyl moiety to form an immobilized biomolecule on a medical device biomaterial surface through covalent bonds.

Another method of the present invention may be employed to crosslink biomolecules, located in solution or on biomaterial surfaces. Such a crosslinked material may be employed as a biomaterial or as a biomaterial coating. In addition, such a crosslinked material may be further modified to contain additional biomolecules. For example, 1,2 dicarbonyl-containing biomolecules may be attached to residual guanidino moieties present in or on the surface of the crosslinked material. Alternatively, guanidino-containing biomolecules may be attached to residual 1,2 dicarbonyl moieties present in or on the surface of crosslinked material. Additionally, biomolecules coated onto a biomaterial surface may be crosslinked according to still another method of the present invention.

DETAILED DESCRIPTION OF THE INVENTION

As used in the specification and claims hereof, the following terms have the particular meanings and definitions set forth below.

I define the term "guanidino moiety" appearing herein to include guanidine, guanidinium, guanidine derivatives such as (RNHC(NH)NHR'), monosubstituted guanidines, monoguanides, biguanides, biguanide derivatives such as (RNHC(NH)NHC(NH)NHR"), and the like. In addition, the term "guanidino moiety" appearing herein may mean any one or more of a guanide alone or a combination of different guanides.

I define the term "biomolecule" appearing herein as a material that engages in a biological activity or which is effective in modulating a biological activity such as eliminating, reducing or enhancing various biological reactions that typically accompany the exposure of bodily tissues or fluids to a biomaterial. Biomaterial-associated reactions include thrombosis, tissue death, tumor formation, allergic reaction, foreign-body reaction (rejection), inflammatory reaction, infection and cellular attachment and growth. Biomolecules suitable for use in the present invention comprise a 1,2 dicarbonyl moiety or a guanidino moiety. A chemical moiety which possesses two carbonyl (C=O) groups located on adjacent carbon atoms is referred to as a 1,2 dicarbonyl moiety. A carbonyl group contains a carbon-oxygen double bond. The term "biomolecule" appearing herein may mean any one or more of a biomolecule alone or a combination of different biomolecules.

I define the term "biomaterial" appearing herein as a material that is substantially insoluble in body fluids and that is designed and constructed to be placed in or onto the body or to contact fluid of the body. Ideally, a biomaterial will not induce undesirable reactions in the body such as thrombosis, tissue death, tumor formation, allergic reaction, foreign-body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains implanted in or in contact with the body. Biomaterials suitable for use in the present invention comprise a 1,2 dicarbonyl moiety or a guanidino moiety.

I define the term "medical device" appearing herein as a device having surfaces that contact bodily tissues and/or fluids in the course of their operation, which fluids are subsequently used in patients. This definition includes within its scope, for example, extracorporeal devices for use in surgery such as blood oxygenators, blood pumps, blood sensors, tubing used to carry blood and the like which contact blood which is then returned to the patient. The definition includes within its scope endoprostheses implanted in blood contact in a human or animal body such as vascular grafts, stents, pacemaker leads, heart valves, and the like that are implanted in blood vessels or in the heart. This definition also includes within its scope devices for temporary intravascular use such as catheters, guide wires, and the like which are placed into blood vessels or the heart for purposes of monitoring or repair.

The present invention has the objective of solving a number of problems associated with the use of medical devices. The present invention includes within its scope a method for covalently attaching biomolecules comprising a 1,2 dicarbonyl moiety to biomaterial surfaces comprising guanidino moieties for use in medical devices. The present invention also provides a method for covalently attaching biomolecules comprising a guanidino moiety to biomaterial surfaces comprising 1,2 dicarbonyl moieties for use in medical devices. The present invention further provides a method for fabricating crosslinked biomaterials or crosslinked biomaterial coatings comprising biomolecules.

Guanidine is the imide of urea, or the amidine of carbamic acid. It is a very strong base with a $pK_a$ of 13.5 in water. The great basicity of guanidine is a result of the stability of the conjugated acid (guanidinium) in water. The positive charge on the guanidinium ion can be spread equally among the three nitrogens by resonance. The guanidinium ion is also quite hydrophilic and is well solvated in aqueous media due to the extensive hydrogen bonding of six potential hydrogen bond donors to the solvent. The partial positive charge of the hydrogen bond donors increases their strength for donation to the negative dipole of water. Crystal structures of simple guanidinium derivatives have revealed several common features. First, the C—N single bond length in an alkyl guanidine is typically shorter than the usual C—N single bond length. Usually, the three C—N bonds in the guanidinium group itself are nearly equal in length with an average of 1.33 A. The three N—C—N bond angles are almost always near 120°.

The guanidinium group's features make it a very attractive moiety for incorporation onto biomaterial surfaces. For example, its high basicity (a $pK_a$ of 13.5 for guanidinium itself) allows it to remain protonated over a much wider range of pH than does the ammonium group. In fact, at physiological pH, all but a small fraction of the guanidine molecules will exist as positively charged species. The guanidinium group's enhanced hydrogen bonding capabilities, typically two linear hydrogen bonds, allow it to form tighter complexes with anions that are capable of hydrogen bonding. In fact, the guanidinium group may form characteristic pairs of zwitterionic hydrogen bonds which provide binding strength by their charge and structural organization by their arrangement. Another feature of guanidines are their ability to react with 1,2 dicarbonyl moieties under mild alkaline conditions to form covalent bonds. The reaction of a guanidino moiety and a 1,2 dicarbonyl moiety is similar to a Schiff base reaction (the reaction between an amine moiety and an aldehyde moiety). In some cases, it may be desirable to use a stabilizing agent such as borate ion ($BO_3^-$) to stabilize the resultant compound.

Biomaterials of the present invention not containing guanidino moieties on their surface may be modified readily to comprise guanidino moieties through a number of methods well known in the art. For example, biomaterials that comprise amines on their surface may be modified to comprise guanidino moieties by reaction with O-methylisourea or S-methylisothiourea to yield substituted guanidines. In fact, guanidino moieties may be synthesized via reaction of an amine with compounds such as S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole. For example, reaction of amines with O-methylisourea, S-methylisourea, S-ethylthiouronium bromide or S-ethylthiouronium chloride, thereby yielding guanidino moieties, are generally completed after 8 hours at 70 degrees Celsius in a solution of sodium hydroxide (NaOH) at pH 10. Reactions of amines with aminoiminomethanesulfonic acid or cyanamide are generally performed at room temperature. Another example is the reaction of an amine with 2-methyl-1-nitroisourea in water to form a nitroguanidine. The nitro group is then easily removed to form a guanidino moiety by hydrogenolysis.

I define the term "guanidino forming agent" appearing herein to include any chemical agent capable of forming a guanidino moiety upon its reaction with a non-guanidino moiety. Examples of guanidino forming agents include S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole. In addition, the term "guanidino forming agent" appearing herein may mean any one or more of a guanidino forming agent or a combination of different guanidino forming agents.

Biomaterials of the present invention not containing amines on their surface may be aminated readily through a number of methods well known in the art. For example, amines may be provided by plasma treating materials with ammonia gas as found in Holmes and Schwartz, "Amination of Ultra-high Strength Polyethylene using Ammonia Plasma", *Composites Science and Technology,* 38, 1–21 (1990). Alternatively, amines may be provided by grafting acrylamide to the substrate followed by chemical modification to introduce amine moieties by methods well known in the art, e.g., Hofmann rearrangement reaction. Polyvinylamines or polyalkylimines may also be covalently attached to polyurethane surfaces according to the method taught by U.S. Pat. No. 4,521,564 to Solomone et al. Alternatively, for example, aminosilane may be attached to the surface as set forth in U.S. Pat. No. 5,053,048 to Pinchuk, a grafted acrylamide-containing polymer may be attached by radiation grafting as set forth in U.S. Pat. No. 3,826,678 to Hoffman et al., a grafted N-(3-aminopropyl) methacrylamide-containing polymer may be attached by ceric ion grafting as set forth in U.S. Pat. No. 5,344,455 to Keogh et al.

There are a number of methods well known in the art to functionalize various moieties to monoguanidines or biguanides (diguanides). A number of these methods are discussed in a book published by John Wiley & Sons Ltd entitled *The Chemistry of Amidines and Imidates,* Vol 2, 485–526 (1991). A number of biguanides and guanidines can also be prepared from ammonium salts as described by Oxley and Short, "Amidines. Part XV. Preparation of Diguanides and Guanidines from Cyanoguanidine and Ammonium Sulphonates", *Journal of the Chemical Society,* 1252–1256 (1951). The covalent attachment of a biomolecule to a guanidino comprising surface may then be accomplished by exposing the modified biomaterial surface to a solution comprising the desired biomolecule.

Molecules which contain at least one guanidino moiety and at least one reactive moiety may be grafted to a biomaterial surface through the reactive moiety. Grafting of molecules such as monomers or polymers to biomaterial surfaces may be accomplished by a number of methods well known to those skilled in the art. For example, monomers or polymers comprising a vinyl reactive moiety may be grafted to biomaterial surfaces using various grafting methods including ceric ion initiation (CeIV), ozone exposure, corona discharge, UV irradiation or ionizing radiation ($^{60}$Co, X-rays, high energy electrons, plasma gas discharge). These grafting methods are examples of how to form free radicals on a biomaterial surface. The free radicals formed thereon initiate the grafting of the vinyl type monomers or polymers. The covalent attachment of a biomolecule to the resultant guanidino comprising surface may then be accomplished by exposing the modified biomaterial surface to a solution comprising the desired biomolecule. There are a variety of reactive moieties the guanidino comprising molecules may possess such as amino moieties, hydroxyl moieties, carboxyl moieties, aldehyde moieties, thio moieties, maleimide moieties, azide moieties, oxazidine moieties, epoxy moieties, isocyanate moieties, succinimide moieties, photochemically reactive moieties, thermochemically reactive moieties or other reactive moieties. An example of a molecule comprising a guanidino moiety and an amino moiety is (4-aminobutyl)guanidine sulfate which is also known as agmatine sulfate.

Compounds such as 1-dodecylguanidine which comprise at least one guanidino moiety and a hydrophobic region may be adsorbed from a solution onto the surface of a hydrophobic biomaterial. The hydrophobic region of the guanidino comprising compound may associate with the hydrophobic biomaterial surface through hydrophobic bonds. Adsorption of compounds comprising hydrophobic regions to hydrophobic biomaterials may be accomplished by a number of methods well known in the art. For example, amphiphilc molecules (molecules which possess a hydrophobic region and a hydrophilic region) may be used to incorporate guanidino moieties on the surface of biomaterials. Preferably, the hydrophilic region of the amphiphilc molecule would comprise the guanidino moiety.

Generally, biomolecules used according to this invention may be, for example, a globular protein, a structural protein, a membrane protein, a cell attachment protein, a protein, a structural peptide, a membrane peptide, a cell attachment peptide, a peptide, an anti-inflammatory agent, an antibody, an antigen, an immunoglobulin, a defense agent, a catalyst, an enzyme, a hormone, a growth factor, a neurotransmitter, a cytokine, a proteoglycan, a toxin, an antibiotic agent, an antibacterial agent, an antimicrobial agent, a regulatory agent, a transport agent, a fibrous agent, a blood agent, a clotting agent, a platelet agent, an antithrombotic agent, an anticoagulant agent, a polysaccharide, a carbohydrate, a fatty acid, a nucleic acid, a DNA segment, RNA segment, a lectin, a drug, a vitamin, a ligand and a dye (which acts as a biological ligand). The biomolecules may be found in nature (naturally occurring) or may be chemically synthesized. Biomolecules which comprise at least one 1,2 dicarbonyl moiety may be covalently attached to a biomaterial surface by one method of the present invention. Biomolecules which comprise at least one guanidino moiety may be covalently attached to a biomaterial surface by another method of the present invention. In addition, complex biomolecule combinations of two or more biomolecules may be covalently attached to a biomaterial surface. If the biomaterial surface comprises both a 1,2 dicarbonyl moiety and a guanidino moiety then both types of biomolecules (biomolecules comprising a 1,2 dicarbonyl moiety and biomolecules comprising a guanidino moiety) may be attached to the biomaterial surface by methods of the present invention. Biomolecules, located in solution or on biomaterial surfaces, may also be crosslinked by another method of the present invention. Such a crosslinked material may be employed as a biomaterial or as a biomaterial coating. In addition, such a crosslinked material may be further modified to contain additional biomolecules.

Biomolecules may be chemically synthesized by a number of methods well known in the art. For example, a number of methods are know for synthesizing proteins or peptides from amino acids including solution (classical) synthesis methods and solid phase (e.g., SPPS) synthesis methods. Peptides of varying length may also be formed by the partial hydrolysis of very long polypeptide chains of proteins. Peptides are short chains constructed of two or more amino acids covalently joined through substituted amide linkages, termed peptide bonds. Two amino acids joined by a peptide bond forms a dipeptide. Three amino acids joined by two peptide bonds forms a tripeptide; similarly, there are tripeptides and pentapeptides. When there are many amino acids joined together, the structure is termed a polypeptide. In general, polypeptides contain less than 100 amino acid residues and proteins contain 100 or more amino acid residues. An amino acid residue comprising a guanidino moiety is arginine.

Some biomolecules are susceptible to conformational changes when brought into contact with a hydrophobic substrate surface. These conformational changes may lead to the exposure of internalized nonpolar groups which may lead to hydrophobic interactions between the biomolecule and the surface. These hydrophobic interactions may cause the exclusion of water molecules that normally surround the biomolecule in solution. This exclusion of water molecules between the biomolecule and the surface strengthens the hydrophobic interaction and may cause further conformational change of the biomolecule. The degree of conformational change a biomolecule experiences may or may not destroy its biological properties. Therefore, one must take into account the hydrophobic nature of the substrate surface when attaching biomolecules which are prone to hydrophobic interactions. In such cases, it is preferred to create a hydrophilic environment on the biomaterial surface, thereby preventing any unwanted hydrophobic interactions between the biomolecule and the surface which may destroy the biological properties of the biomolecule.

There are a number of surface-derivatization techniques (e.g., grafting techniques) well known in the art for creating hydrophilic substrate surfaces. For example, techniques based on ceric ion initiation, ozone exposure, corona discharge, UV irradiation and ionizing radiation ($^{60}$Co, X-rays, high energy electrons, plasma gas discharge) are known.

Substrates that may be modified according to one method of the present invention include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers such as polyamides, polycarbonates, polyethers, polyesters, polyolefins including polyethylenes and polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, minerals or ceramics such as hydroxapatite, human or animal protein or tissue such as bone, skin, teeth, collagen, laminin, elastin or fibrin, organic materials such as wood, cellulose or compressed carbon, and other materials such as glass, and the like. Biomaterials of the present invention made using these materials may be coated or uncoated, and derivatized or underivatized.

One method of the invention may be used to modify substrates of any shape or form including tubular, sheet, rod and articles of proper shape for use in a number of medical devices such as vascular grafts, aortic grafts, arterial, venous, or vascular tubing, vascular stents, dialysis membranes, tubing or connectors, blood oxygenator tubing or membranes, ultrafiltration membranes, intra-aortic balloons, blood bags, catheters, sutures, soft or hard tissue prostheses, synthetic prostheses, prosthetic heart valves, tissue adhesives, cardiac pacemaker leads, artificial organs, endotracheal tubes, lens for the eye such as contact or intraocular lenses, blood handling equipment, apheresis equipment, diagnostic and monitoring catheters and sensors, biosensors, dental devices, drug delivery systems, or bodily implants of any kind.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent or other publication cited herein is incorporated by reference, as if each such patent or publication were individually incorporated by reference herein.

I claim:

1. A method of forming a coating on a surface of a medical device, the coating imparting improved biocompatibility characteristics to the surface, the surface being suitable for contacting bodily tissues or fluids in or temporarily removed from a living mammalian subject, the method comprising:
   (a) providing the medical device, the medical device having a suitable biomaterial forming the surface, a guanidino moiety being disposed on the surface;
   (b) providing a biomolecule, the biomolecule comprising a 1,2 dicarbonyl moiety; and
   (c) combining the 1,2 dicarbonyl moiety with the guanidino moiety to form covalent bonds, the covalent bonds immobilizing the biomolecule on the surface, the immobilized biomolecule forming the coating.

2. The method of claim 1, further comprising the addition of a stabilizing agent.

3. The method of claim 2, wherein the stabilizing agent is borate ion.

4. The method of claim 1, wherein the medical device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

5. The method of claim 1, wherein the guanidino moiety is an arginine amino acid.

6. The method of claim 1, wherein the biomolecule is a naturally occurring biomolecule.

7. The method of claim 1, wherein the biomolecule is a chemically synthesized biomolecule.

8. The method of claim 1, wherein the biomolecule is selected from the group consisting of a globular protein, a structural protein, a membrane protein, a cell attachment protein, a protein, a structural peptide, a membrane peptide, a cell attachment peptide, a peptide, an anti-inflammatory agent, an antibody, an antigen, an immunoglobulin, a defense agent, a catalyst, an enzyme, a hormone, a growth factor, a neurotransmitter, a cytokine, a proteoglycan, a toxin, an antibiotic agent, an antibacterial agent, an antimicrobial agent, a regulatory agent, a transport agent, a fibrous agent, a blood agent, a clotting agent, a platelet agent, an antithrombotic agent, an anticoagulant agent, a polysaccharide, a carbohydrate, a fatty acid, a nucleic acid, a DNA segment, RNA segment, a lectin, a drug, a vitamin and a ligand.

9. The method of claim 1, wherein at least a portion of the surface forms at least one of a tube, a rod, a membrane, a balloon, a bag and a sheet.

10. The method of claim 1, wherein the surface comprises at least one of a biocompatible material selected from the group consisting of metal, titanium, titanium alloys, tinnickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

11. A method of forming a coating on a surface of a medical device, the coating imparting improved biocompatibility characteristics to the surface, the surface being suitable for contacting bodily tissues or fluids in or temporarily removed from a living mammalian subject, the method comprising:
    (a) providing the medical device, the device having a suitable biomaterial forming the surface, a 1,2 dicarbonyl moiety being disposed on the surface;
    (b) providing a biomolecule, the biomolecule comprising a guanidino moiety; and
    (c) combining the guanidino moiety with the 1,2 dicarbonyl moiety to form covalent bonds, the covalent bonds immobilizing the biomolecule on the surface, the immobilized biomolecule forming the coating.

12. The method of claim 11, further comprising the addition of a stabilizing agent.

13. The method of claim 12, wherein the stabilizing agent is borate ion.

14. The method of claim 11, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

15. The method of claim 11, wherein the guanidino moiety is an arginine amino acid.

16. The method of claim 11, wherein the biomolecule is a naturally occurring biomolecule.

17. The method of claim 11, wherein the biomolecule is a chemically synthesized biomolecule.

18. The method of claim 11, wherein the biomolecule is selected from the group consisting of a globular protein, a structural protein, a membrane protein, a cell attachment protein, a protein, a structural peptide, a membrane peptide, a cell attachment peptide, a peptide, an anti-inflammatory agent, an antibody, an antigen, an immunoglobulin, a defense agent, a catalyst, an enzyme, a hormone, a growth factor, a neurotransmitter, a cytokine, a proteoglycan, a toxin, an antibiotic agent, an antibacterial agent, an antimicrobial agent, a regulatory agent, a transport agent, a fibrous agent, a blood agent, a clotting agent, a platelet agent, an antithrombotic agent, an anticoagulant agent, a polysaccharide, a carbohydrate, a fatty acid, a nucleic acid, a DNA segment, RNA segment, a lectin, a drug, a vitamin and a ligand.

19. The method of claim 11, wherein at least a portion of the surface forms at least one of a tube, a rod, a membrane, a balloon, a bag and a sheet.

20. The method of claim 11, wherein the surface comprises at least one of a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

21. A method of forming a coating on a surface of a medical device, the coating imparting improved biocompatibility characteristics to the surface, the surface being suitable for contacting bodily tissues or fluids in or temporarily removed from a living mammalian subject, the method comprising:
    (a) providing the medical device, the device having a suitable biomaterial forming the surface, an amine moiety being disposed on the surface;
    (b) combining the amine moiety with a guanidino forming agent to form a guanidino moiety on the surface;
    (c) providing a biomolecule, the biomolecule comprising a 1,2 dicarbonyl moiety; and
    (d) combining the 1,2 dicarbonyl moiety with the guanidino moiety to form covalent bonds, the covalent bonds immobilizing the biomolecule on the surface, the immobilized biomolecule forming the coating.

22. The method of claim 21, further comprising the addition of a stabilizing agent.

23. The method of claim 22, wherein the stabilizing agent is borate ion.

24. The method of claim 21, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

25. The method of claim 21, wherein the guanidino forming agent is selected from the group consisting of S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole.

26. The method of claim 21, wherein the guanidino moiety is an arginine amino acid.

27. The method of claim 21, wherein the biomolecule is a naturally occurring biomolecule.

28. The method of claim 21, wherein the biomolecule is a chemically synthesized biomolecule.

29. The method of claim 21, wherein the biomolecule is selected from the group consisting of a globular protein, a structural protein, a membrane protein, a cell attachment protein, a protein, a structural peptide, a membrane peptide, a cell attachment peptide, a peptide, an anti-inflammatory agent, an antibody, an antigen, an immunoglobulin, a defense agent, a catalyst, an enzyme, a hormone, a growth factor, a neurotransmitter, a cytokine, a proteoglycan, a toxin, an antibiotic agent, an antibacterial agent, an antimicrobial agent, a regulatory agent, a transport agent, a fibrous agent, a blood agent, a clotting agent, a platelet agent, an antithrombotic agent, an anticoagulant agent, a polysaccharide, a carbohydrate, a fatty acid, a nucleic acid, a DNA segment, RNA segment, a lectin, a drug, a vitamin and a ligand.

30. The method of claim 21, wherein at least a portion of the surface forms at least one of a tube, a rod, a membrane, a balloon, a bag and a sheet.

31. The method of claim 21, wherein the surface comprises at least one of a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

32. A method of forming a coating on a surface of a medical device, the coating imparting improved biocompatibility characteristics to the surface, the surface being suitable for contacting bodily tissues or fluids in or temporarily removed from a living mammalian subject, the method comprising:
   (a) providing the medical device, the device having a suitable biomaterial forming the surface, a 1,2 dicarbonyl moiety being disposed on the surface;
   (b) providing a biomolecule, the biomolecule comprising an amine moiety;
   (c) combining the amine moiety with a guanidino forming agent to form a guanidino moiety; and
   (d) combining the guanidino moiety with the 1,2 dicarbonyl moiety to form covalent bonds, the covalent bonds immobilizing the biomolecule on the surface, the immobilized biomolecule forming the coating.

33. The method of claim 32, further comprising the addition of a stabilizing agent.

34. The method of claim 33, wherein the stabilizing agent is borate ion.

35. The method of claim 32, wherein the device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

36. The method of claim 32, wherein the guanidino forming agent is selected from the group consisting of S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole.

37. The method of claim 32, wherein the guanidino moiety is an arginine amino acid.

38. The method of claim 32, wherein the biomolecule is a naturally occurring biomolecule.

39. The method of claim 32, wherein the biomolecule is a chemically synthesized biomolecule.

40. The method of claim 32, wherein the biomolecule is selected from the group consisting of a globular protein, a structural protein, a membrane protein, a cell attachment protein, a protein, a structural peptide, a membrane peptide, a cell attachment peptide, a peptide, an anti-inflammatory agent, an antibody, an antigen, an immunoglobulin, a defense agent, a catalyst, an enzyme, a hormone, a growth factor, a neurotransmitter, a cytokine, a proteoglycan, a toxin, an antibiotic agent, an antibacterial agent, an antimicrobial agent, a regulatory agent, a transport agent, a fibrous agent, a blood agent, a clotting agent, a platelet agent, an antithrombotic agent, an anticoagulant agent, a polysaccharide, a carbohydrate, a fatty acid, a nucleic acid, a DNA segment, RNA segment, a lectin, a drug, a vitamin and a ligand.

41. The method of claim 32, wherein at least a portion of the surface forms at least one of a tube, a rod, a membrane, a balloon, a bag and a sheet.

42. The method of claim 32, wherein the surface comprises at least one of a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

43. A method of forming a crosslinked coating on a surface of a medical device, the coating being suitable for contacting bodily tissues or fluids in or temporarily removed from a living mammalian subject, the method comprising:
   (a) providing a first biomolecule, the first biomolecule comprising a 1,2 dicarbonyl moiety;
   (b) providing a second biomolecule, the second biomolecule comprising a guanidino moiety;
   (c) combining the guanidino moiety with the 1,2 dicarbonyl moiety to form covalent bonds, the covalent bonds crosslinking the two materials together to form a crosslinked biomaterial;
   (d) providing a medical device surface: and
   (e) immobilizing the crosslinked biomaterial on the surface, the crosslinked biomaterial forming the coating.

44. The method of claim 43, further comprising the addition of a stabilizing agent.

45. The method of claim 44, wherein the stabilizing agent is borate ion.

46. The method of claim 43, wherein the first biomolecule is selected from the group consisting of an anticoagulant, an antithrombotic, a clotting agent, a platelet agent, an anti-inflammatory, an antibody, an immunoglobulin, a defense agent, an enzyme, a hormone, a growth factor, a neurotransmitter, a cytokine, a globular protein, a blood agent, a regulatory agent, a transport agent, a fibrous agent, a structural protein, a membrane protein, a cell attachment protein, a structural peptide, a membrane peptide, a cell attachment peptide, a proteoglycan, a toxin, an antibiotic, and a ligand.

47. The method of claim 43, wherein the guanidino moiety is an arginine amino acid.

48. The method of claim 43, wherein the second biomolecule is selected from the group consisting of an anticoagulant, an antithrombotic, a clotting agent, a platelet agent, an anti-inflammatory, an antibody, an immunoglobulin, a defense agent, an enzyme, a hormone, a growth factor, a neurotransmitter, a cytokine, a globular protein, a blood agent, a regulatory agent, a transport agent, a fibrous agent, a structural protein, a membrane protein, a cell attachment protein, a structural peptide, a membrane peptide, a cell attachment peptide, a proteoglycan, a toxin, an antibiotic, and a ligand.

49. The method of claim 43, wherein the medical device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a cell seeding medical device, a cell binding medical device, a cell separating medical device, a vascular graft, a stent, a heart valve, a tissue glue and a temporary intravascular medical device.

50. The method of claim 43, wherein at least a portion of the crosslinked biomaterial forms at least one of a tube, a rod, a membrane, a balloon, a bag and a sheet.

51. The method of claim 43, wherein the crosslinked biomaterial is combined with a third biomolecule.

52. The method of claim 51, wherein the third biomolecule is selected from the group consisting of an anticoagulant, an antithrombotic, a clotting agent, a platelet agent, an anti-inflammatory, an antibody, an immunoglobulin, a defense agent, an enzyme, a hormone, a growth factor, a neurotransmitter, a cytokine, a globular protein, a blood agent, a regulatory agent, a transport agent, a fibrous agent, a structural protein, a membrane protein, a cell attachment protein, a structural peptide, a membrane peptide, a cell attachment peptide, a proteoglycan, a toxin, an antibiotic, and a ligand.

53. A method of forming a crosslinked coating on a surface of a medical device, the coating imparting improved biocompatibility characteristics to the surface, the surface being suitable for contacting bodily tissues or fluids in or temporarily removed from a living mammalian subject, the method comprising:
(a) providing the medical device, the device having a suitable biomaterial forming the surface, a first guanidino moiety being disposed on the surface;
(b) providing two or more biomolecules, the biomolecules comprising a second guanidino moiety and a 1,2 dicarbonyl moiety;
(c) combining the biomolecules with the surface; and
(d) allowing the first and second guanidino moieties to combine with the 1,2 dicarbonyl moieties to form covalent bonds, the bonds immobilizing and crosslinking the biomolecules on the surface, the immobilized and crosslinked biomolecules forming the coating.

54. The method of claim 53, further comprising the addition of a stabilizing agent.

55. The method of claim 54, wherein the stabilizing agent is borate ion.

56. The method of claim 53, wherein the medical device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

57. The method of claim 53, wherein the first or second guanidino moiety is an arginine amino acid.

58. The method of claim 53, wherein the biomolecules are naturally occurring biomolecules.

59. The method of claim 53, wherein the biomolecules are chemically synthesized biomolecules.

60. The method of claim 53 wherein the biomolecules are selected from the group consisting of a globular protein, a structural protein, a membrane protein, a cell attachment protein, a protein, a structural peptide, a membrane peptide, a cell attachment peptide, a peptide, an anti-inflammatory agent, an antibody, an antigen, an immunoglobulin, a defense agent, a catalyst, an enzyme, a hormone, a growth factor, a neurotransmitter, a cytokine, a proteoglycan, a toxin, an antibiotic agent, an antibacterial agent, an antimicrobial agent, a regulatory agent, a transport agent, a fibrous agent, a blood agent, a clotting agent, a platelet agent, an antithrombotic agent, an anticoagulant agent, a polysaccharide, a carbohydrate, a fatty acid, a nucleic acid, a DNA segment, RNA segment, a lectin, a drug, a vitamin and a ligand.

61. The method of claim 53, wherein at least a portion of the surface forms at least one of a tube, a rod, a membrane, a balloon, a bag and a sheet.

62. The method of claim 53, wherein the surface comprises at least one of a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

63. The method of claim 53, wherein the first or second guanidino moiety is formed by combining an amine moiety with a guanidino forming agent.

64. The method of claim 63, wherein the guanidino forming agent is selected from the group consisting of S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide, dicyandiamide, 3,5-dimethyl-1-guanylpyrazole nitrate and 3,5-dimethyl pyrazole.

65. A method of forming a crosslinked coating on a surface of a medical device, the coating imparting improved biocompatibility characteristics to the surface, the surface being suitable for contacting bodily tissues or fluids in or temporarily removed from a living mammalian subject, the method comprising:
(a) providing the medical device, the device having a suitable biomaterial forming the surface, a first 1,2 dicarbonyl moiety being disposed on the surface;
(b) providing two or more biomolecules, the biomolecules comprising a guanidino moiety and a second 1,2 dicarbonyl moiety;
(c) combining the biomolecules with the surface; and
(d) allowing the guanidino moieties to combine with the first and second 1,2 dicarbonyl moieties to form covalent bonds, the bonds immobilizing and crosslinking the biomolecules on the surface, the immobilized and crosslinked biomolecules forming the coating.

66. The method of claim 65, further comprising the addition of a stabilizing agent.

67. The method of claim wherein the stabilizing agent is borate ion.

68. The method of claim 65, wherein the medical device is selected from the group consisting of a blood-contacting medical device, a tissue-contacting medical device, a bodily fluid-contacting medical device, an implantable medical device, an extracorporeal medical device, a blood oxygenator, a blood pump, tubing for carrying blood, an endoprosthesis medical device, a vascular graft, a stent, a pacemaker lead, a heart valve, temporary intravascular medical device, a catheter and a guide wire.

69. The method of claim 65, wherein the guanidino moiety is an arginine amino acid.

70. The method of claim 65, wherein the biomolecules are naturally occurring biomolecules.

71. The method of claim 65, wherein the biomolecules are chemically synthesized biomolecules.

72. The method of claim 65, wherein the biomolecules are selected from the group consisting of a globular protein, a structural protein, a membrane protein, a cell attachment protein, a protein, a structural peptide, a membrane peptide, a cell attachment peptide, a peptide, an anti-inflammatory agent, an antibody, an antigen, an immunoglobulin, a defense agent, a catalyst, an enzyme, a hormone, a growth factor, a neurotransmitter, a cytokine, a proteoglycan, a toxin, an antibiotic agent, an antibacterial agent, an antimicrobial agent, a regulatory agent, a transport agent, a fibrous agent, a blood agent, a clotting agent, a platelet agent, an antithrombotic agent, an anticoagulant agent, a polysaccharide, a carbohydrate, a fatty acid, a nucleic acid, a DNA segment, RNA segment, a lectin, a drug, a vitamin and a ligand.

73. The method of claim 65, wherein at least a portion of the surface forms at least one of a tube, a rod, a membrane, a balloon, a bag and a sheet.

74. The method of claim 65, wherein the surface comprises at least one of a biocompatible material selected from the group consisting of metal, titanium, titanium alloys, tin-nickel alloys, shape memory alloys, aluminum oxide, platinum, platinum alloys, stainless steel, MP35N stainless steel, elgiloy, stellite, pyrolytic carbon, silver carbon, glassy carbon, polymer, polyamide, polycarbonate, polyether, polyester, polyolefin, polyethylene, polypropylene, polystyrene, polyurethane, polyvinyl chloride, polyvinylpyrrolidone, silicone elastomer, fluoropolymer, polyacrylate, polyisoprene, polytetrafluoroethylene, rubber, ceramic, hydroxapatite, human protein, human tissue, animal protein, animal tissue, bone, skin, teeth, collagen, laminin, elastin, fibrin, wood, cellulose, compressed carbon and glass.

75. The method of claim 65, wherein the guanidino moiety is formed by combining an amine moiety with a guanidino forming agent.

76. The method of claim 75, wherein the guanidino forming agent is selected from the group consisting of S-ethylthiouronium bromide, S-ethylthiouronium chloride, O-methylisourea, O-methylisouronium sulfate, O-methylisourea hydrogen sulfate, S-methylisothiourea, 2-methyl-1-nitroisourea, aminoiminomethanesulfonic acid, cyanamide, cyanoguanide.

* * * * *